United States Patent [19]

Matkovich

[11] Patent Number: 4,731,061
[45] Date of Patent: Mar. 15, 1988

[54] APPARATUS AND METHOD FOR REDUCING RISK OF CONTAMINATION AND DELIVERING TO A PATIENT PHARMACEUTICALLY-ACCEPTABLE MATERIAL

[75] Inventor: Vlado I. Matkovich, Glen Cove, N.Y.

[73] Assignee: Pall Corporation, East Hills, N.Y.

[21] Appl. No.: 63,798

[22] Filed: Jun. 24, 1987

Related U.S. Application Data

[63] Continuation of Ser. No. 763,917, Aug. 8, 1985, abandoned.

[51] Int. Cl.$^4$ .............................................. A61M 5/325
[52] U.S. Cl. .................................. 604/263; 604/256; 604/244; 604/111
[58] Field of Search ............... 604/111, 113, 151, 244, 604/252, 256, 263, 406

[56] References Cited

U.S. PATENT DOCUMENTS

| | | | |
|---|---|---|---|
| 2,901,112 | 8/1959 | Nafturn et al. | 604/252 |
| 3,217,710 | 11/1965 | Beall et al. | 128/214 |
| 3,342,179 | 9/1967 | Ellmann | 128/214.2 |
| 3,677,242 | 7/1972 | Shaye | 604/252 |
| 3,994,412 | 11/1976 | Difiglio | 604/111 |
| 4,022,191 | 5/1977 | Jamshidi | 604/263 |
| 4,144,718 | 3/1979 | Williams | 62/180 |
| 4,240,481 | 12/1980 | Bayham | 150/8 |
| 4,248,223 | 2/1981 | Turner et al. | 128/214 C |
| 4,249,923 | 2/1981 | Walda | 62/394 |
| 4,305,443 | 12/1981 | Bayham | 150/8 |
| 4,334,536 | 6/1982 | Pfleger | 128/218 |
| 4,340,052 | 7/1982 | Dennehey et al. | 128/247 |
| 4,346,703 | 8/1982 | Dennehey et al. | 128/213 A |
| 4,416,280 | 11/1983 | Carpenter et al. | 128/399 |
| 4,430,077 | 2/1984 | Mittleman et al. | 604/111 |
| 4,457,749 | 7/1984 | Bellotti et al. | 604/29 |

FOREIGN PATENT DOCUMENTS

| | | |
|---|---|---|
| 0062148 | 2/1982 | European Pat. Off. |
| 0057001 | 8/1982 | European Pat. Off. |
| 1949038 | 4/1970 | Fed. Rep. of Germany |
| 2629717 | 1/1978 | Fed. Rep. of Germany |
| 2716783 | 10/1978 | Fed. Rep. of Germany |
| 328845 | 3/1958 | Switzerland |

Primary Examiner—C. Fred Rosenbaum
Assistant Examiner—Colleen Reilly
Attorney, Agent, or Firm—Leydig, Voit & Mayer

[57] ABSTRACT

A unit is provided comprising a filter assembly, a cap and connector assembly to substantially reduce the risk of contaminants entering the flow of material delivered to a patient. The cap and connector assembly portion protects an administration kit from contamination during the priming of the kit. A first portion of the cap closes off the material flow route through the connector, but can be removed by tearing it away from the second portion at a weak area, opening the flow route and allowing the administration kit to be primed. As the system is primed, the second portion of the cap protects the outer surface of the connector. After the administration set has been primed, the second portion of the cap is removed, exposing the outer walls of the connector for mating with a complementary connector. The housing includes three ports for material flow. First and second ports are adjacently positioned on one side of the housing to recirculate the material without the material passing through the filter material within the housing. The third port is located on the housing such that material flow between the third port and either the first or second port requires the material to flow through the filter material. Also provided is a Y-connector for a recirculating administration kit and a housing for a filter which prevents contamination in a recirculating administration kit caused by counterflow in the recirculation line.

3 Claims, 6 Drawing Figures

APPARATUS AND METHOD FOR REDUCING RISK OF CONTAMINATION AND DELIVERING TO A PATIENT PHARMACEUTICALLY-ACCEPTABLE MATERIAL

This is a continuation of co-pending application Ser. No. 763,917, filed on Aug. 8, 1985, now abandoned.

TECHNICAL FIELD OF THE INVENTION

The invention generally relates to the administration of fluid by an intravenous feeding apparatus and, more particularly, to the administration of cardioplegia fluid in a chilled and uncontaminated condition.

BACKGROUND

In many types of medical treatment, such as blood transfusions, intravenous feeding and the administration of medicinal solutions, it is necessary to introduce liquids into a patient, sometimes in rather large amounts. When this is done, it is quite important that absolutely no contaminants such as particulates and bacteria be permitted to pass into the patient with the liquid, because of the danger of injury or infection, with possibly fatal consequences. It is also necessary to exclude air, in order to prevent the development of an embolism in the patient.

The liquids themselves that are to be administered can easily be made clean and are assumed to remain so until administration. The main possibility of contamination arises, however, when the storage receptacle is to be connected with the administration set. The connection must be made under such conditions that no contaminants or bacteria can enter the system at the connection.

Liquid administration apparatus of this type, particularly intravenous liquid administration apparatus, normally requires a filter, to ensure that undesirable or foreign contaminants in gaseous or particulate form not be administered. Such filters are connected in series between the reservoir or supply of liquid to be administered and the administration set that passes the liquid into the patient.

One particular source of potential contamination of the fluid occurs during the process of priming the filter of the administration set before connecting it to the catheter for delivery of the fluid to the patient. Usually, the extension line from a filter, which is received by a complementary connector on the catheter, ends in a cap to keep the extension line sterile. Before the fluid can be delivered to the patient, the filter must be primed with the fluid in order to insure microscopic air bubbles are not initially trapped in the filter and later delivered to the patient.

To prime the filter, the cap at the end of the extension line is removed and the fluid is allowed to flow through the delivery line, through the filter and spill into a convenient receptacle. As the fluid leaves the end of the tubing of the extension line, drops may form on the outside of the connector either by capillary attraction of the liquid as it flows out the end of the tubing or simply from the splashing of the liquid as it leaves the end of the tubing. Since the released fluid is exposed to the air, the drops of fluid on the outside of the connector of the extension line may be contaminated. When the connector is used to join the extension line to the catheter, the contaminated fluid may leak into the flow to the patient.

Another particular source of possible contamination exists during open heart surgery. Heart surgery often requires that the surgeon terminate the functioning of the heart without damaging the heart muscle. This is accomplished by injecting a chilled cardioplegia fluid through a catheter into the aortic root of the heart, thereby causing it to cease pumping.

Before the surgical procedure begins, the flow of the chilled cardioplegia fluid is stopped. During the surgical procedure, the cardioplegia solution may be re-applied several times to insure the heart does not spontaneously start.

Because the cardioplegia fluid in the delivery line of the administration set begins to warm between applications of the fluid to the heart, recirculating systems have been developed which return the fluid from the delivery line to the source of refrigeration when the fluid is not flowing to the heart. By recirculating the fluid when it is not in use, the fluid in the delivery line remains chilled. Therefore, when the cardioplegia fluid is re-applied to the heart during surgery, the delivery line does not intitially deliver warmed fluid.

Typically, in such a recirculating system, a delivery line feeds the cardioplegia fluid to the heart from an output port of a fluid reservoir. In order to recirculate the fluid, the delivery line includes a Y-connector (i.e., a three-port connector) which serves to divert the fluid to a recirculation line when the portion of the delivery line downstream from the Y-connector is closed. The portion of the delivery line downstream of the Y-connector is commonly referred to as the extension line which is inserted into the catheter. When the extension line is closed, the fluid flows from the delivery line into the recirculation line and back into the reservoir.

Located along the delivery line are a pump and a cooling unit for pumping and cooling, respectively, the cardioplegia fluid. Also located in the delivery line is a filter for removing contaminates from the reservoir which may be carried by the fluid. Typically, the filter is primed in the manner described earlier.

During surgery, the recirculation of the cardioplegia fluid may be interrupted and restarted. If the flow is stopped, the effect of gravity causes some fluid from the recirculation line to back-flow into the delivery line. In the sterile environment of the operating room, the reservoir (e.g., plastic bag) for the cardioplegia fluid is considered a source of contamination. Since the recirculation line returns the fluid back to the reservoir, the possibility exists that contaminated fluid may be gravity fed into the delivery line when the pump of the recirculating system is stopped. Moreover, even while the cardioplegia fluid is flowing in the recirculation line, there is some counterflow in the line. This counterflow creates the risk of providing a route for contaminants to bypass the filter of the administration set and enter the extension line of the set which leads to the patient.

It is the primary object of the invention to provide an improved delivery system for intravenous liquid which does not have the foregoing contamination problems.

More specifically, it is an object of the invention to provide an improved cap for the end of the extension line of an administration set which allows the set to be primed without causing contamination of the connector joining the administration set to the catheter of the patient.

It is another object of the invention to prevent contamination caused by the back-flow or counterflow of fluid in the recirculation line of a system for delivering fluid to a patient.

It is yet another object of the invention to provide the foregoing objectives without significantly increasing the cost or complexity of the administration set.

Other objects and advantages of the invention will be apparent from the following detailed description and the accompanying drawings.

The invention provides a filter assembly and a cap and connector assembly which function in a complementary manner to substantially reduce the risk of contaminants entering the flow of material delivered to a patient from a reservoir and through an administration kit. In order to prime the administration kit, the cap of the cap and connector assembly comprises first and second portions integrally attached to form a bacteria-tight and leak-tight seal in a press fit engagement with the connector, wherein the first and second portions are joined by an annular weak area. The first portion of the cap closes off the material flow route provided by the connector, but the first portion can be removed by tearing it away from the second portion at the weak area, thereby opening the material flow route and allowing the administration kit to be primed. As the system is primed, the second portion of the cap protects the outer surface of the connector from contamination by material flow. After the administration set has been primed, the second portion of the cap is removed, thereby exposing the outer walls of the connector for mating with a complementary connector. Thus, the connector may be received by a complementary connector without risk that the outer walls of the connector carry material which may work its way into the flow to the patient.

When an administration set includes a recirculation line, the invention includes a filter assembly whose housing forms a Y-connection joining the delivery line, recirculation line and the extension line. The housing of the filter assembly comprises top and bottom sections joined by side sections so as to provide a chamber of filter material. First and second fluid ports on the top section of the housing cooperate to recirculate fluid without the fluid passing through the filter material within the housing. A third port located on the bottom section of the housing communicates with the first and second port such that a flow route between either the first and third ports for the second and third ports require the fluid to flow through the filter material. The foregoing structure simultaneously provides a Y-connector for the recirculating administration kit and a housing for a filter. Because the structure of the housing places to filter downstream of the recirculating flow, the patient is protected from possible contamination resulting from back-flow or counterflow in the recirculation line.

BRIEF DESCRIPTION OF THE DRAWINGS

While the invention will be described in connection with a recirculating cardioplegia administration set, it will be understood that it is not intended to be limited to such a set. On the contrary, the invention is intended to cover all administration sets which require priming before introducing the liquid to a patient.

DETAILED DESCRIPTION OF THE PREFERRED EMBODIMENT

Figure 1:
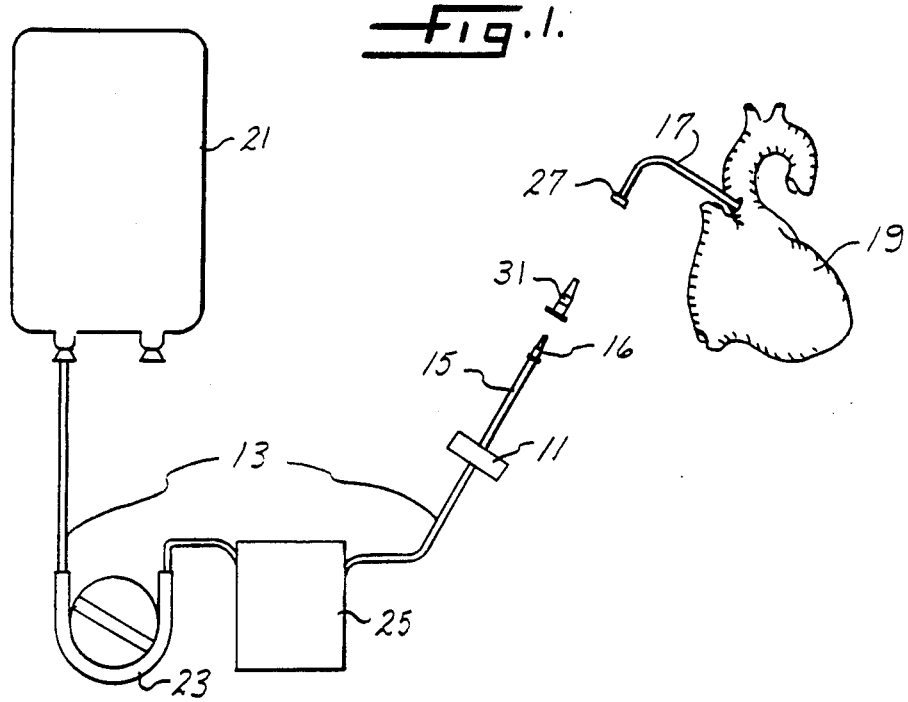
FIG. 1 is a schematic diagram of a nonrecirculating cardioplegia administration set incorporating a cap according to the invention covering the connector located at the end of the extension line of the set.

In a non-recirculating cardioplegia system as illustrated in FIG. 1, a filter 11 connects a delivery line 13 to an extension line 15 to compromise an administration set. The free end of the extension line 15 includes an integral connector 16 for joining the system to a catheter 17 which is inserted into the patient's heart 19 at the base of the aorta. Chilled cardioplegia fluid is supplied to the heart 19 from a fluid supply reservoir 21 via a pump 23 and a cooling unit 25. In a conventional manner, the pump 23 initiates flow of the cardioplegia fluid through the cooling unit 25 and filter 11. As the fluid leaves the cooling unit 25, it is at a reduced temperature suitable for aiding in the stopping of heart motion.

Before the administration set is connected to the catheter 17 for delivery of the chilled fluid to the patient's heart 19, the delivery line 13 and filter 11 must be primed in order to purge it of all microscopic air bubbles. Following the typical approach, the extension line 15 is held by the physician so that the filter 11 is upside down, i.e., the fluid enters at the bottom and flows out the top. By positioning the filter 11 upside down, any microscopic air bubbles are allowed to escape out the end of the extension line 15 as the level of the fluid in the filter rises. The administration set is fully primed when the fluid spills from the connector 16.

In accordance with one important aspect of the invention, a cap 31 for the connector 16 is provided which substantially reduces the risk of contaminating the cardioplegia fluid during the priming process. The cap forms a bacteria-tight and leak-tight seal over the connector 16 which is partially removable so as to allow priming of the administration set yet continues to protect the connector during the priming process so as to prevent contamination of the fluid delivered to the patient. Upon completion of the priming process, the remaining portion of the cap is removed, thereby totally exposing the underlying connector 16 for its mating with a complementary connector 27 of the catheter 17.

Figure 2:
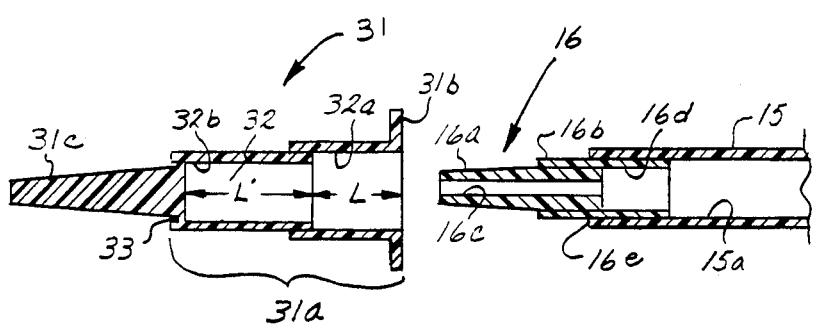
FIG. 2 is an enlarged, cross-sectional view of the cap and connector illustrated in FIG. 1.

Referring to FIG. 2, the connector 16 is connected in a conventional manner into the end of the flexible tubing of the extension line 15. The outer wall of the connector 16 is cylindrical in shape and in two sections of distinct diameters, with the smaller diameter section 16a located at the free end of the connector and tapered in order to facilitate mating of the connector with the connector 27 of the catheter 17. In the larger diameter section 16b, the diameter is substantially constant along the length of the section with a portion of the section being received by the extension line 15.

In order to provide for fluid flow from the extension line 15, the connector 16 includes a dual-diameter cylindrical bore for routing fluid. The smaller diameter bore 16c runs the length of the smaller section 16a and continues into the larger section 16b. A larger diameter bore 16d joins with the smaller diameter section 16c to provide a transition between the small cross section of bore 16c and the much greater cross section of the bore 15a in the extension line 15. Because the smaller bore 16c extends into the area of larger outer diameter 16b, the walls of the connector 16 are thickest in this area, thereby improving the structural integrity of the connector.

In order for the cap 31 to provide a bacteriatight seal over the connector 16, the main portion 31a of the cap includes a bore 32 which substantially conforms to the shape and size of the outer walls 16a and 16b of the connector 16. Specifically, the bore 32 is of a dual-diameter with the first diameter section 32a having a diameter only slightly greater than the diameter of section 16b of the connector 16 such that the cap 31 and connector are fitted in a pressed engagement. The length L of the bore section 32a is slightly longer than that of the connector section 16b in order to insure the cap 31 fully fits over the connector 16 so that the end of the cap 31b rests on the base 16e of the connector.

Similarly, a smaller, second diameter section 32b of the bore 32 has a diameter similar to that of the outside wall of the smaller section 16a of the connector 16. Because the cap 31 is sufficiently secured to the connector 16 by the press-fit engagement provided by the bore section 32a and the outer wall 16b, the bore section 32b is slightly larger than the diameter of the connector section 16a, thereby easing the fitting of the cap over the connector. As with bore section 32a, the length L' of bore section 32b is slightly more than connector section 16a in order to assure an easy fit of the cap 31.

The bore 32 of the cap 31 is closed by a tip 31c of the cap which is secured to the main portion 31a of the cap by way of a thin wall 33 which forms an annular weak area joining the tip and the main portion of the cap. The tip 31c and its connecting thin wall 33 close the end of the bore 32, thereby enabling the cap 31 to provide a bacteria-tight and leak-tight seal when fitted over the connector 16, yet the weakness of the wall provides an area at which the tip can be separated from the main portion 31a in order to transform the bore 32 into a through passageway for fluid.

Figure 3:
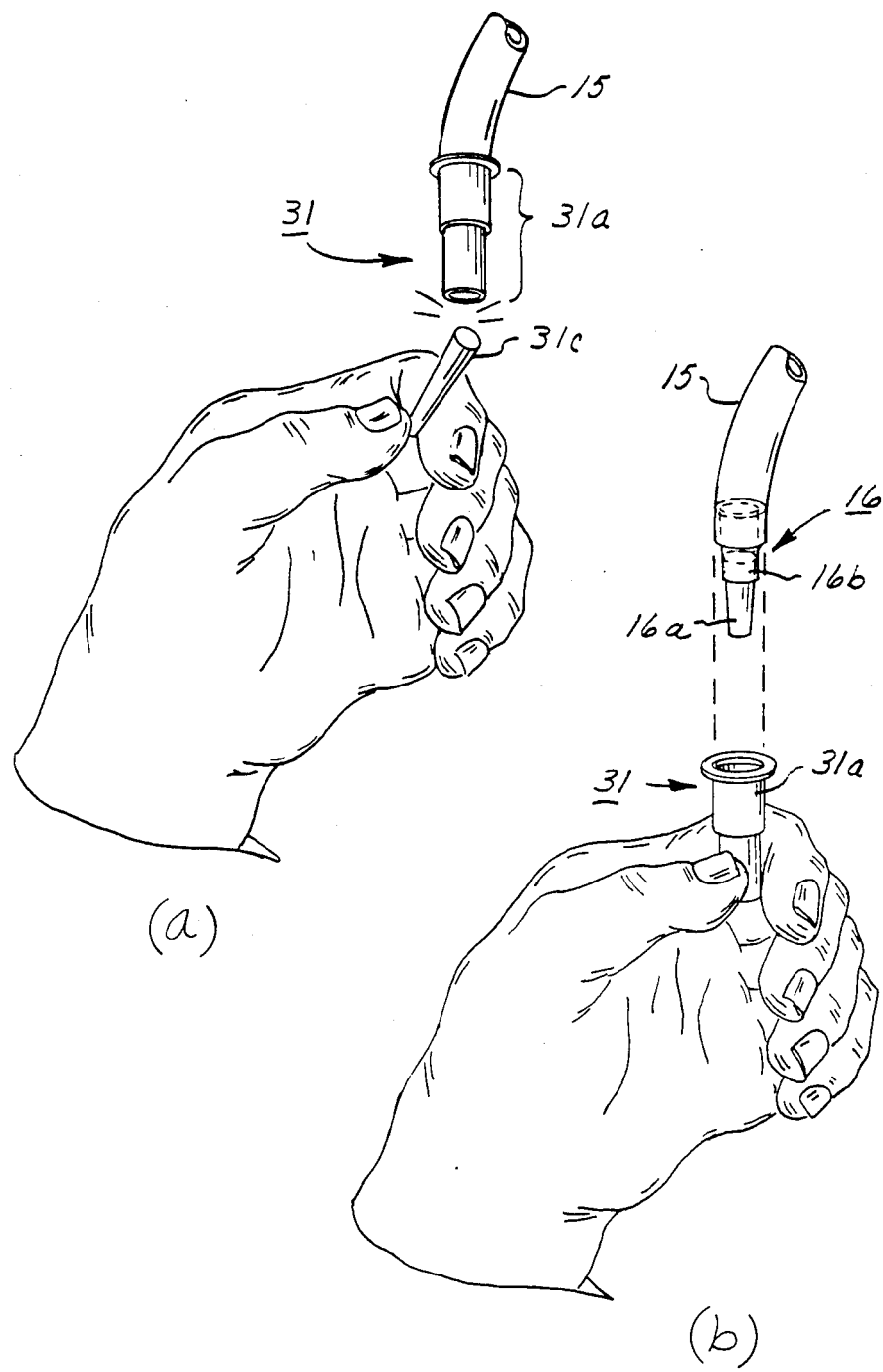
FIG. 3a is an enlarged view of the cap of FIG. 1 illustrating the removal of a break-off tip portion of the cap in order to prime the cardioplegia administration set.
FIG. 3b is the cap of FIG. 3a illustrating the removal of the remaining portion of the cap after the cardioplegia system has been primed.

In keeping with the invention, the administration set is primed with cardioplegia fluid by first breaking off the tip 31c of the cap 31 as illustrated in FIG. 3a. As the delivery line 13 and filter 11 are filled with fluid by action of the pump 23, any air trapped in the set is allowed to escape through the passageway 16a and 16b of the connector 16 which has been unblocked by the removal of the tip 31b. When the fluid flows from connector 16, the set is fully primed and ready to be connected to the connector 27 of the catheter 17. Because the main portion 31a of the cap 31 is retained in its position during priming of the set, the outer walls 16a and 16b of the connector 16 remain protected from contact with contaminated fluid. Removal of the main portion 31a of the cap 31 as illustrated in FIG. 3b exposes the underlying walls 16a and 16b of the connector 16 which are not contaminated and may join with the connector 27 without risk of possibly introducing contaminated cardioplegia fluid into the flow to the patient.

From the foregoing, it can be appreciated that the connector 16 may be formed from transparent rigid plastic material, such as a polycarbonate or polypropylene. The cap 31 is preferably formed of resilient plastic material such as polyethylene, polypropylene, polymethyl pentene-1, polyvinyl chloride, and vinyl chloride-vinylidene chloride copolymers. The cap 31 can be formed in the disclosed configuration by casting or molding, such as by extrusion or injection molding. The thin wall 33 or weak annular area between the main portion 31a of the cap 31 and the tip 31c can also be formed by casting or molding. For simplicity of construction, the cap 31 is best formed in one piece, but it is also possible to form the cap in two pieces, the tip 31c forming one piece, and being bonded integrally to the main portion 31a by solvent bonding, by heat-fusing or by spin welding.

The cap 31 may be incorporated into a recirculating system as well as the non-recirculating system of FIG. 1. In a recirculating delivery system for cardioplegia fluid, the administration set typically includes a Y-connector which joins the delivery line and extension line to a recirculation line. When delivery of the cardioplegia fluid to the patient is stopped, it recirculates back to the reservoir via the Y-connector and the recirculation line.

Figure 4:
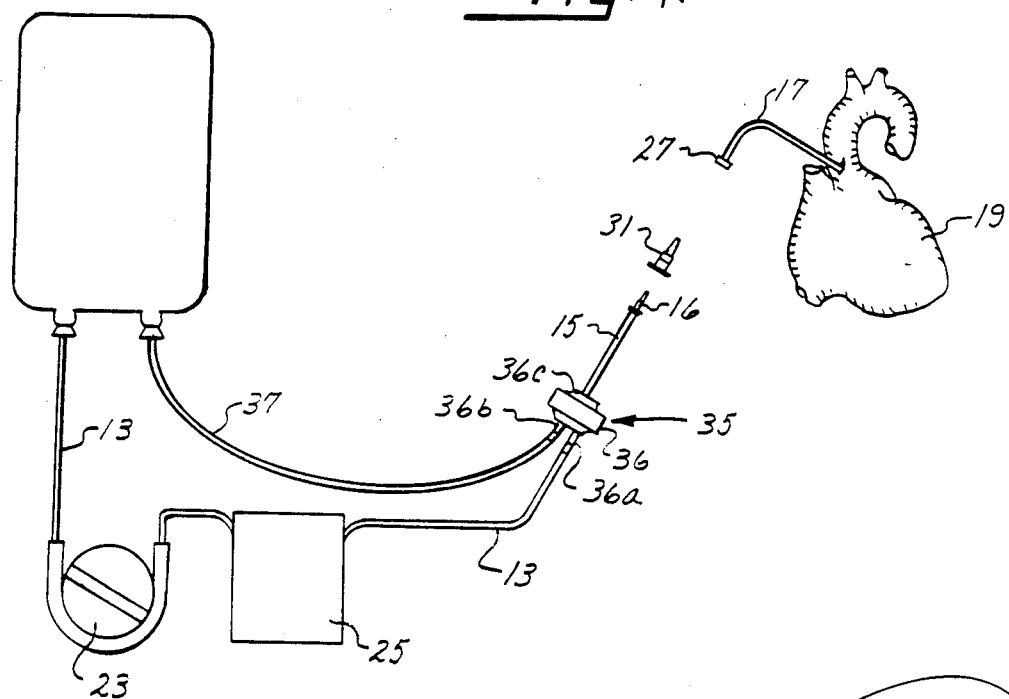
FIG. 4 is a schematic diagram of a recirculating cardioplegia system incorporating the cardioplegia filter and the extension cap in accordance with the invention.

In accordance with another important aspect of the invention, the rilter 11 in the non-recirculating system of FIG. 1 is replaced in the recirculating system of FIG. 4 by a filter 35 which replaces the traditional Y-connector and which prevents contaminiated fluid from entering the flow to the patient by way of back-flow or counterflow in the recirculating line 37. In order to provide the function of a Y-connector, the housing 36 of the filter 35 includes three ports; two of the ports 36a and 36b are located on one side of the housing 36 such that fluid flow between the two ports does not require the fluid pass through the filter material (not shown) contained in the housing. The third port 35c is located on a side of the housing 36 of the filter 35 which may receive flow from one of the two other ports only by passage of the fluid through the filter material.

In the administration set of the recirculating system of FIG. 4, the two ports 36a and 36b on one side of the housing 36 connect to the delivery line 13 and the recirculation line 37. The third port 35c is mated to the extension line 15. By alternatively closing either the recirculation line 37 or the extension line 15, the cardioplegia fluid can be routed to the patient (recirculation line closed) or routed back to the supply reservoir 21, pump 23 and cooling unit 25 (extension line closed).

With the extension line 15 closed, the cardioplegia fluid enters the first port 36a and travels along the top of the housing 36 to the adjacent port 36b. Because the port 36b is on the same side of the housing 36 as port 36a, the filter material is virtually untouched by the recirculating fluid. Therefore, the filter 35 is not needlessly filtering fluid which is only recirculating, and the filter is not resisting flow and adding work to the pump 23 as it would if the pump were required to pump fluid through the filter during recirculation.

More important than the functioning of the housing 36 as a Y-connector in a recirculating system is the repositioning of the filter 35 so that the recirculation route of the fluid is isolated from the extension line 15 by the filter 35. Placement of the filter 35 as shown in FIG. 4 insures only filtered and uncontaminated fluid is delivered to the patient.

Figure 5:
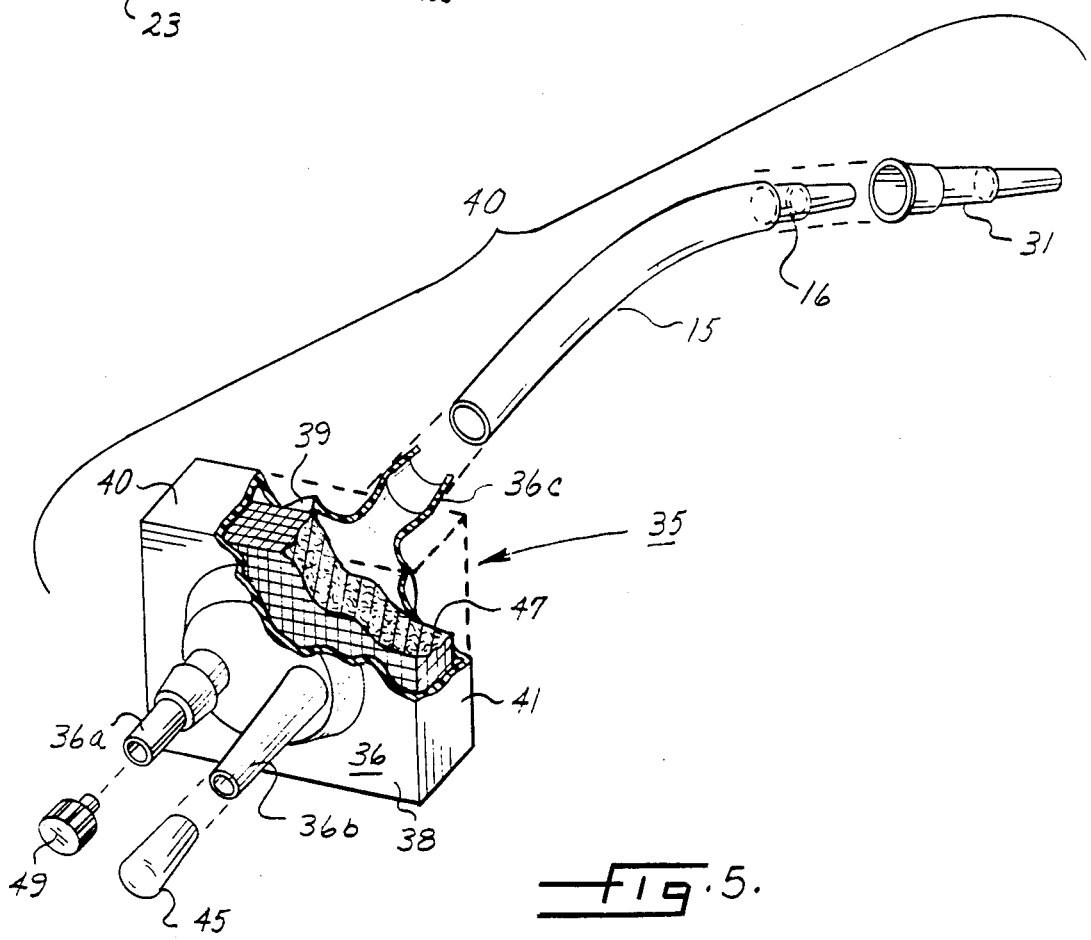
FIG. 5 is a partially-sectioned, perspective view of the cardioplegia filter according to the invention, including a two port top section and a single port bottom section with the bottom section having an integral extension line for the single bottom port which ends in a connector and cap assembly according to the invention.

Preferably, the filter 35, extension line 15, connector 16 and cap 31 are manufactured as a unit 40 as illustrated in FIG. 5. By securing the extension line 15 to the third port 36c of the filter housing 36 during the manufacturing process, the surgeon need only connect the delivery line 13 and the recirculation line 37 to complete the application set. Because the surgeon only makes connections upstream of the filter 35 (with the exception of the connector 16), the risk of contamination during set up is substantially reduced. Of course, the connector 16, which is downstream of the filter 35, is protected by the cap 31 in keeping with the invention. By providing a simple protective cover 45 for the second port 36b, the unit 40 may be adapted to a non-recirculating system and provide the same advantages.

Although the housing 36 of the filter 35 is illustrated as square in its shape with top and bottom areas 38 and 39, respectively, larger than the areas of each of the four sides (only two sides 40 and 41 are shown in FIG. 5), the particular shape of the housing is unimportant as long as it provides the necessary flow routes between the three ports 35a–c as previously described. The particular flow material 47 used may be that disclosed in U.S. Pat. No. 4,340,479, assigned to the assignee of the present invention.

For the construction of the particular housing illustrated in FIG. 5, the bottom 39 and two opposing sides, a separate top 38 and two separate remaining sides are first formed as individual pieces and then bonded together by conventional means to form the completed housing 36 which encloses the filter material and protects it from contamination. Examples of possible bonding techniques are ultrasonic welding, adhesives or a mutual solvent. Finally, the housing 36 is preferably made from rigid or semirigid plastic such as polypropylene, polyethylene or polyamide. A cap 49 protects the port 36a prior to the use of the unit.

From the foregoing, it will be appreciated that the invention provides a device for an adminstration set, easily adapted for use in either recirculating or non-recirculating delivery systems, which provide enhanced protection for the patient from contaminated fluids entering the flow to the patient. The complementary functions of the three-port filter 35 and the cap 31 for the connector 16 allow the unitary construction of FIG. 5 to provide the potential to improve the adminisrration set of any delivery system.

I claim:

1. In a recirculating system for delivering a pharmeceutically-acceptable material, a filter assembly forming a Y-connection and comprising:
    a housing having top and bottom sections joined by a side section so as to provide a chamber of filter material;
    first and second ports on the top section of the housing which cooperate to recirculate the material without the material passing through the filter material; and
    a third port on the bottom section of the housing for communication with the first and second ports so as to provide a flow route for the material through the filter material, the third port of the housing includes an extension line integrally secured at a first end to the third port so as to provide a conduit for flow of material exiting said third port, said extension line having a second end mated to a connector protected by a cap, wherein said cap includes means for protecting said connector from contamination by capillary attraction or splashing of material as it flows from said connector during priming of said filter assembly, said means comprising first and second generally cylindrical sections joined by a thin annular area that enables said second section to be torn away from said first section so as to allow the priming of said filter assembly, said first section having a central opening for allowing said first section to fit over the outer surface of said connector and for removing said first section from said connector so as to expose said outer surface for mating with a complementary connector and said second section having means for blocking flow of material through said connector when said cap is mated to said connector.

2. A filter assembly as set forth in claim 1 wherein said central opening of said first section has a dual-diameter for mating with a dual-diameter of said outer surface of said connector so as to provide a press-fit engagement of said cap on said connector, each diameter of the dual-diameter central opening having a length slightly greater than the length of the corresponding diameter of said outer surface of said connector.

3. In a first system for administrating pharmaceutically-acceptable material, having a first connector for attaching the first system to a second system by way of a complementary second connector, an apparatus for preventing contamination of said material and for use in priming said first system before attaching it to said second system, said apparatus comprising a cap for protecting said connector and having a first generally cylindrical section for protecting and outer surface of said connector from contamination by capillary attraction or splashing of material as it flows from said connector during priming of said system, said first section having a central opening for allowing it to fit over said outer surface of said connector and for removing said first section from said connector so as to expose said outer surface for mating with said complementary second connector, said cap also having a second section that includes means for blocking the flow of material through said first connector when said cap is mated to said first connector, said first and second sections being joined by a thin annular area that enables said second section to be torn away from said first section so as to allow the priming of said first system while said first section remains fitted over said first connector.

* * * * *